United States Patent [19]

Collins et al.

[11] 4,174,346

[45] Nov. 13, 1979

[54] PROCESS FOR PREPARING ORGANOTIN COMPOUNDS

[75] Inventors: John D. Collins, Albrighton; Donald A. Wood, Warley, both of England

[73] Assignee: Albright & Wilson Limited, Warley, both of England

[21] Appl. No.: 802,626

[22] Filed: Jun. 2, 1977

[30] Foreign Application Priority Data

Jun. 8, 1976 [GB] United Kingdom ............... 23666/76

[51] Int. Cl.$^2$ ............................................... C07F 7/22
[52] U.S. Cl. ................................................. 260/429.7
[58] Field of Search ..................................... 260/429.7

[56] References Cited

U.S. PATENT DOCUMENTS

| | | | |
|---|---|---|---|
| 3,297,732 | 1/1967 | Banks | 260/429.7 |
| 3,402,189 | 9/1968 | Natoli | 260/429.7 |
| 3,607,891 | 9/1971 | Kushlefsky et al. | 260/429.7 |
| 3,647,833 | 3/1972 | Reifenberg et al. | 260/429.7 |
| 3,789,057 | 1/1974 | Reifenberg et al. | 260/429.7 |

FOREIGN PATENT DOCUMENTS 1067437  5/1967  United Kingdom ................ 260/429.7
1070742  6/1967  United Kingdom ................ 260/429.7

Primary Examiner—Helen M. S. Sneed
Attorney, Agent, or Firm—Frishauf, Holtz, Goodman & Woodward

[57] ABSTRACT

Tricycloalkyltin chlorides e.g. tricyclohexyltin chlorides, which may be converted to the fungicide tricyclohexyl hydroxide, are made by reacting an organic tricycloalkyltin, in which the organic is not cycloalkyl and cycloalkyl is optionally substituted cyclohexyl, with organic tin trihalide.

41 Claims, No Drawings

PROCESS FOR PREPARING ORGANOTIN COMPOUNDS

This invention relates to a process for preparing organotin compounds, in particular tricycloalkyltin chlorides.

Tricyclohexyltin hydroxide is a fungicide which is prepared by alkaline hydrolysis of tricyclohexyltin chloride. Tricyclohexyltin chloride may be obtained by an inverse Grignard process by adding cyclohexyl magnesium chloride to stannic chloride or by a disproportionation reaction of an organo tricyclohexyltin with a substantially equimolar amount of stannic chloride in solution to form tricyclohexyltin chloride and an organotin trichloride. The organotin trichloride byproduct may be separated from the tricyclohexyltin chloride after distillation of the solvent either, when the former is a liquid, by filtration of the latter from a suspension in the former, or by extraction of the former with aqueous hydrochloric acid leaving the tricyclohexyltin chloride as an insoluble solid. The organotricyclohexyltin is prepared by reacting cyclohexyl magnesium chloride with the organotin trichloride.

We have now found a process for preparing the tricycloalkyltin chloride and hence the hydroxide in which the byproducts and tricycloalkyltin compound at the chloride or hydroxide stage can be separated easily.

The present invention provides a process for preparing a tricycloalkyltin compound, which comprises reacting an organotricycloalkyltin of formula $RSnR''_3$ wherein R'' is a cycloalkyl group, which is cyclohexyl or cyclohexyl substituted by at least one inert substituent, R is an alkyl, alkenyl, aralkyl or aryl group, with an organotin trichloride of formula $R'SnCl_3$ wherein R' is an organic group, e.g. as defined for R or is a cycloalkyl group as defined above, to form a mixture comprising a tricycloalkyltin chloride and a diorganotin dichloride.

The organo group R in the organo tricycloalkyltin is an alkyl group, e.g. of 1–18 carbon atoms, preferably 1–8, e.g. 3–8 carbon atoms, such as methyl, ethyl, butyl, octyl or dodecyl, an alkenyl group, e.g. of 2 to 8 carbon atoms such as vinyl, allyl, or methallyl, an aralkyl group, e.g. of 7 to 19 carbon atoms, e.g. benzyl or betaphenyl ethyl, or an aryl group, e.g. an aromatic hydrocarbyl group such as one of 6–18 carbon atoms, preferably 6–8 carbon atoms such as phenyl, tolyl, or xylyl, or a halogen substituted derivative, such as a chlorine derivative, of one of these aromatic hydrocarbyl groups, e.g. chlorophenyl. Preferably R is an alkyl group, e.g. of 1–8 carbon atoms or aryl group, in particular a phenyl, butyl, methyl or octyl group.

The organo group R' in the organotin trichloride may be any organic group, e.g. any of the groups mentioned above for R, or a cycloalkyl group, e.g. a group as defined for R''. Preferably R' is an alkyl group of 1–8 carbon atoms. R and R' are advantageously the same, and especially n-butyl groups.

The cycloalkyl group R'' is a cyclohexyl group or a cyclohexyl group substituted by at least one inert substituent, e.g. 1–3 substituents but preferably only one such substituent, the substituents being for example an alkyl group of 1 to 5 carbon atoms, e.g. a methyl or ethyl group, as in the 2- or 3-methyl cyclohexyl groups.

The organotin trichloride and organo tricycloalkyltin are heated together in the presence or absence of an inert liquid diluent which is often a solvent for the reactants. The reactants are heated usually at a temperature of at least 100° C., e.g. 100°–200° C., preferably 110°–180° C. and especially 130°–180° C. such as 130°–150° C. Examples of suitable solvents are liquid aliphatic, cyclo aliphatic and aromatic hydrocarbons, such as toluene and xylene, cyclohexane, and liquid paraffins, or inert chlorinated aliphatic hydrocarbons such as dichloroethane and tetrachloroethane, and inert liquid chlorinated aromatic hydrocarbons such as chlorobenzene. Particularly suitable solvents are those whose boiling points are such that the reaction can be performed in refluxing solvent, e.g. xylene. Preferably the solvent is absent, and preferably the temperature is 120°–160° C.

The reaction time depends on the presence or absence of solvent, and the reaction temperature, and is usually in the range 0.1–24 hours, but as examples times of 1–5 hours at 130°–170° C., especially 130°–150° C. in the absence of a solvent and 4–24 hours at 130°–190° C., especially 160°–190° C. in the presence of a solvent may be suitable.

The organotricycloalkyltin and organotin trichloride are usually reacted in a molar ratio of 0.5:1 to 2:1, e.g. 0.8:1 to 1.2:1, e.g. about 1:1.

The organotricycloalkyltin compound used as reactant to prepare the tricycloalkyltin chloride may be prepared as described in British Patent specification No. 1,262,986, using the general technique described in U.S. Pat. No. 3,010,979. A cycloalkyl magnesium halide is reacted in a 3:1 molar ratio with an organotin trichloride usually in an ether solvent such as tetrahydrofuran.

The organotin trichloride reactant used to prepare the tricycloalkyltin chloride may be prepared by processes known or described in the chemical literature, for example, by reaction of tetraorganotins with stannic chloride in a 1:3 molar ratio or by reaction of stannic chloride with a Grignard reagent in a 1:1 molar ratio. The compounds are usually purified, e.g. by distillation or crystallization before use.

Alternatively, the organotin trichloride of formula $R'SnCl_3$, wherein R' is as defined for R, may be prepared in situ by reaction of organotricycloalkyltin of formula $RSnR''_3$ with stannic chloride usually in a substantially equimolar ratio to form a mixture of tricycloalkyltin chloride and organotin trichloride. While it is possible to separate the tricycloalkyltin chloride at this stage and then carry out the process of the invention with the remaining organotin trichloride, it is preferred to use the mixture as such for reaction with organotricycloalkyltin in the process of this invention. The further reaction may be performed by adding extra organotricycloalkyltin to the above mixture but preferably enough of organotricycloalkyltin is mixed with the stannic chloride at the start for that which is unreacted in the first step to react in the process of the invention in the second step. Thus in a preferred process the organotricycloalkyltin and stannic chloride are mixed in a molar ratio of at least 1.5:1 e.g. 1.5–2.5:1, such as 1.8–2.2:1 and preferably about 2:1, and the reaction performed to produce eventually a mixture comprising tricycloalkyltin and diorganotin dichloride. The organotricycloalkyltin and stannic chloride, often in an inert liquid diluent as described above, may be mixed usually at less than 100° C., to form a reaction composition comprising tricycloalkyltin chloride, organotin trichloride and unreacted organotricycloalkyltin and then the temperature raised above 100° C., e.g. 110°–180° C., preferably 130°–150° C., as described above for the process of the invention to form said reaction mixture comprising tricycloalkyltin chloride and diorganotin chloride; alternatively the organotricycloalkyltin and stannic chloride may be mixed and reacted directly at above 100° C., e.g. at 130°–150° C. and this constitutes another aspect of this invention. When the organotricycloalkyltin is reacted with stannic chloride in a molar ratio of at least 1.5:1 the product comprises a mixture of tricycloalkyltin chloride and diorganotin dichloride in a molar ratio of at least 1.5:1, usually 2:1, the proportions aiding separation of the tricycloalkyltin chloride in comparison with the product from the reaction of organo tricycloalkyltin and organotrichloride in which the two main components are produced in about equimolar amounts.

Whether the mixture of the two main components, i.e., tricycloalkyltin chloride and diorganotin dichloride, is made from organotricycloalkyltin and organotintrichloride or stannic chloride, the two components may be separated at this stage by distillation of the diorganotin dichloride if it has a low enough boiling point, e.g. dimethyltin dichloride or dibutyltin chloride enabling the diorganotin dichloride to be recovered cleanly. Alternatively, the two compounds in the mixture may be separated by means of their different solubilities, i.e., by preferential crystallization of the tricycloalkyltin chloride from a solution of the mixture in, e.g. isopropanol, enabling the tricyclohexyltin chloride to be recovered cleanly.

However, the mixture of tricycloalkyltin chloride and diorganotin dichloride need not be separated at this stage and may be hydrolysed by heating with an aqueous base to form a mixture of tricycloalkyltin hydride and diorganotin oxide or hydroxide. The aqueous base may be an aqueous solution of an alkali metal or alkaline earth metal hydroxide, preferably sodium or potassium hydroxide or an aqueous solution of ammonia or an aqueous solution of suspension or a tertiary amine, e.g. a trialkylamine such as one with 1-6 carbon atoms in each alkyl group, preferably triethylamine. The amount of the hydroxide is sufficient to hydrolyse completely the tin chlorides to the corresponding oxide or hydroxides. The aqueous base is heated with the mixture of diorganotin dichloride and tricycloalkyltinchloride in an inert liquid organic diluent usually a water immiscible one. The solvent which is stable to the base under the reaction conditions may be one of the inert diluents that may be used in the preparation of the mixture though lower boiling solvents such as cyclo hexane are preferred. When a diluent is used in the production of the mixture of organotin chloride, the solution of reaction mixture as produced may be mixed with the base, avoiding any isolation step. Alternatively the diluent may be different in the two stages, the first diluent being removed by evaporation at the end of the reaction. If the mixture were prepared in the absence of solvent, then one of the above mentioned solvents is added. In any event, the water immiscible diluent for the hydrolysis is preferably one in which the diorganotin oxdie is insoluble, e.g. for dibutyltin oxide, cyclohexane or an aromatic hydrocarbon of 6-9 carbon atoms such as toluene or xylene is suitable whereas for diphenyltin oxide a paraffinic solvent is applicable. The hydrolysis is carried out by heating the mixture, diluent and aqueous base, preferably at 50° to 140° C., or the boiling point of the overall liquid whichever is the lower. Hydrolysis times of 1-4 hours are often suitable.

At the end of the hydrolysis, the hydrolysis reaction mixture usually comprises an aqueous and organic phase and a precipitate of the diorganotin oxide. The precipitate may be separated before or after separation of the phases. The organic phase which contains the tricycloalkyltin hydroxide and is substantially free of the diorganotin oxide, may be concentrated to dryness and then recrystallized or otherwise purified, e.g. by washing with acetone, as necessary or desired. Alternatively, the organic phase can be concentrated sufficiently to cause deposition of crystals of the tricycloalkyltin hydroxide, which are then separated.

In a preferred form, the present invention provides a process for preparing a tricycloalkyltin hydroxide, which comprises in a first step reacting an organo tricycloalkyltin of formula $RSnR_3''$ with an organotin trichloride of formula $R'SnCl_3$, wherein R, R' and R" are as defined above, to produce a mixture of a tricycloalkyltin chloride and a diorganotin dichloride, in a second step treating this mixture in solution in an inert liquid water immiscible organic diluent with an aqueous base to form an organic phase comprising tricycloalkyltin hydroxide, an aqueous phase and a precipitate of diorganotin oxide or hydroxide, in a third step separating the tricycloalkyltin hydroxide from the organic phase; the precipitate and aqueous phase are separated, before or after separation of the organic and aqueous phases. This process is advantageous in giving a clean separation between the tricycloalkyltin hydroxide and the diorganotin oxide, which is obtained in a form easy to use as an intermediate.

In order to maximize separate recovery of the tricycloalkyl chloride and dialkyltin dichloride, it is often desirable to effect separation of the majority of one component at the chloride stage, e.g. tricyclohexyltin chloride by crystallization or dibutyltin dichloride by distillation and then convert the residue containing the majority of the unisolated component to the corresponding hydroxide or oxide by hydrolysis as described. In this way, the mother liquors from the crystallization of tricyclohexyltin chloride, which contain mostly diorganotin dichloride, e.g. dibutyltin dichloride but also some tricyclohexyltin chloride, may be hydrolysed in the presence of the solvent in which the diorganotin oxide is insoluble to give the three phase mixture of solvent layer comprising tricyclohexyltin hydroxide, aqueous layer and precipitate of diorganotin oxide, which may be separated as described above.

Thus, in a preferred form of the invention the reaction mixture of tricycloalkyltin chloride and diorganotin dichloride is treated to separate one of the two components substantially from the other to leave a residue, which is then treated in solution in an inert liquid water immiscible solvent with an aqueous base to form an organic phase comprising tricycloalkyltin hydroxide an aqueous phase and a precipitate of diorganotin oxide or hydroxide and separating the precipitate and recovering the tricycloalkyltin hydroxide.

In a most preferred embodiment of the invention, mixtures of tricyclohexyltin chloride and dialkyltin dichloride wherein the alkyl groups are the same and have 1-8 carbon atoms, e.g. butyl are obtained by heating at 110°–180° C. alkyl tricyclohexyltin and alkyltin trichloride in a molar ratio of 0.8:1 to 1.2:1, e.g. 1:1, the reaction being especially carried out in the absence of a liquid diluent, or by heating at 110°–180° said alkyltricyclohexyltin and stannic chloride in a molar ratio of at least 1.5:1, e.g. 1.8–2.2:1 and especially about 2:1 (or the product of reacting the same at less than 100° C.).

The reaction to form the tricycloalkyltin chloride often also produces dicycloalkyltin dichloride as by-product, but the amounts are often very small.

The isolated tricyclohexyltin chloride may be used as such or separately converted to the hydroxide. The isolated tricycloalkyltin hydroxide may be used as a fungicide. The separated diorganotin dichloride or diorganotin oxide or hydroxides are intermediates for making stabilizers for halogen containing polymers or other biocides.

The invention is illustrated in the following Examples in which butyl tricyclohexyltin was prepared from butyltin trichloride and cyclohexyl magnesium chloride as described in Example 5 (a).

EXAMPLE 1

A solution of equimolar amounts of butyl tricyclohexyltin and butyltin trichloride in commercial xylene was refluxed for 22½ hours. Analysis of the reaction mixture obtained showed that the reaction had gone to about 89% completion to form predominantly tricyclohexyltin chloride and dibutyltin dichloride.

EXAMPLE 2

A solution of butyl tricyclohexyltin (42 g) and butyltin trichloride (28 g) in 200 ml of a solvent sold under the Trade Name Shellsol A, with b.p. 172° C., was refluxed by 7 hours, after which time the reaction has gone to at least 93% completion. The solvent was evaporated by heating under vacuum at a temperature of up to 100° C. at 1 mm Hg leaving residue (72.1 g), which was dissolved in xylene (200 ml). A mixture of the xylene solution of the residue and an aqueous solution of sodium hydroxide (14.3 g) in water (200 ml) was stirred at 85° C. for two hours. A precipitate comprising dibutyltin oxide and a little butyl stannoic acid was filtered from the hot mixture leaving a filtrate which was evaporated to dryness. The evaporated residue was slurried with acetone (ca. 100 ml) and the suspension filtered to give a precipitate (32.5 g) which was 92.3% tricyclohexyltin hydroxide and 7.7% dicyclohexyltin oxide. 3.2 g of a further fraction containing 50% of tricyclohexyltin hydroxide was obtained by concentration of the acetone filtrate and filtration.

EXAMPLE 3

Tricyclohexylbutyltin (42.0 g) and redistilled butyltin trichloride (28.0 g) were mixed together and stirred as a melt under nitrogen at 150° C. for 3.5 hours. The product (70.0 g) was quickly cooled to 100° C. and by Vapour Phase Chromatography (VPC) the reaction was found to be substantially complete.

The above product was dissolved in xylene (200 ml) and to this solution was added an aqueous solution of sodium hydroxide (14.3 g) dissolved in distilled water (200 ml). This mixture was refluxed for two hours with stirring, then cooled to 60° C., and then a precipitate of dibutyltin oxide and butyl stannoic acid was filtered off and the filter cake washed leaving a solid (24.0 g). The filtrate was an organic phase and an aqueous phase which were separated. The organic phase was evaporated to dryness in a rotary evaporator at 15 mm and up to 90° C. leaving a crystalline solid (37.2 g) which was 93.5% tricyclohexyltin hydroxide and 5.9% dicyclohexyltin oxide expressed by weight as the corresponding chlorides.

EXAMPLE 4

Tricyclohexylbutyltin (42.5 g) and butyltin trichloride (28.3 g) were heated together at 150° C. for two hours, 50 minutes. After this time the reaction mixture on analysis by VPC was found to contain 54.0% tricyclohexyltin chloride, 0.4% tricyclohexylbutyltin, 42.9% dibutyltindichloride and 2.1% dicyclohexyltin dichloride. The mixture was cooled and recrystallized from isopropanol to yield 34.8 g (86.4% yield) of a solid product, whose analysis was 97.7%, tricyclohexyltin chloride, 1.7% dicyclohexyltin dichloride and 0.6% dibutyltindichloride.

EXAMPLE 5

(a) Preparation of Butyltricyclohexyltin

An initiation mix of cyclohexyl chloride (0.76 g), cyclohexyl bromide (0.61 g) and tetrahydrofuran (6.3 g) was added to magnesium (5.52 g) in a reactor purged with nitrogen. After initiation, cyclohexyl chloride (25.7 g), tetrahydrofuran (50.9 g) and cyclohexane (21.8 g) were added over two hours and the mixture refluxed for 1.5 hours. n-Butyltin trichloride (20 g) was added over 45 minutes under reflux and then the mixture refluxed for 1.5 hours. After cooling the mass was treated with a mixture of concentrated hydrochloric acid (2.5 g) and water (48.8 g) with stirring for 0.5 hours and then allowed to separate into an aqueous and organic layer. The organic layer was evaporated at up to 130°–140° C. under 50 mm Hg pressure to leave butyltricyclohexyltin.

(b) Preparation of Tricyclohexyltinchloride n-Butyltin trichloride (19.5 g) was added to the above butyltricyclohexyltin in the reactor and the mass kept at 130°–140° C. for about four hours, by which time analysis by VPC showed that the reaction was substantially complete. The mass was treated with isopropanol (76 g) and after refluxing for 1 hour, the liquid was allowed to cool to room temperature whereupon tricyclohexyltin chloride crystallized out. The slurry of crystals was filtered and the filter cake washed to leave a solid in 82% yield, whose analysis was 97.3% tricyclohexyltin chloride and 2.7% dicyclohexylbutyltin chloride. Of the organotin content of the mother liquor, 73.7% was dibutyltin dichloride, 8.0% butyltintrichloride and 8.6% tricyclohexyltin chloride.

EXAMPLE 6

To a stirred solution of butyl tricyclohexyltin (42.5 g) in benzene (50 ml) was added dropwise over 1 hour a solution of stannic chloride (13.05 g) in benzene (50 ml). After stirring for a further 1.5 hours, analysis of the reaction mixture showed the presence of tricyclohexyltin chloride, butyltin trichloride and unreacted butyltricyclohexyltin. The mixture was heated to evaporate the benzene and the residue kept at 130°–140° C. for four hours. When the mixture had cooled, it was crystallized from isopropanol to give 85% yield of the product containing 99.4% of tricyclohexyltin chloride.

We claim:

1. A process for preparing a tricycloalkyltin compound, which comprises reacting at a temperature of between 110° C. and 180° C.
   an organotricycloalkyltin of formula $RSnR_3''$, wherein $R''$ is a cycloalkyl group selected from the group consisting of cyclohexyl and cyclohexyl substituted by at least one inert substituent, and R is a radical selected from the group consisting of alkyl, alkenyl, aralkyl and aryl groups,
with an organotin trichloride of formula R'SnCl$_3$, wherein R' is an organic group,
the molar ratio of said organotricycloalkyltin to said organotin trichloride being between 0.8:1 and 1:1.2, to form a mixture comprising tricycloalkyltin chloride and a diorganotin dichloride.

2. A process according to claim 1 wherein the reaction is performed at between 130° C. and 150° C.

3. A process according to claim 1 wherein the reaction is carried out in the absence of a liquid diluent.

4. A process according to claim 1 wherein R is an alkyl group of 1-8 carbon atoms.

5. A process according to claim 1 wherein R' is an alkyl group of 1-8 carbon atoms.

6. A process according to claim 3 wherein R and R' are the same alkyl group of 1-8 carbon atoms.

7. A process according to claim 6 wherein R and R' are butyl groups.

8. A process according to claim 1 wherein the tricycloalkyltin chloride is separated from the diorganotin dichloride by preferential crystallization of the tricycloalkyltin chloride from a solution of the mixture.

9. A process according to claim 8 wherein the tricycloalkyltin chloride is crystallized from isopropanol solution.

10. A process according to claim 1 wherein a mixture of tricycloalkyltin chloride with the diorganotin dichloride in solution in an inert liquid water immiscible organic diluent is treated with an aqueous base to form an organic phase comprising tricycloalkyltin hydroxide, an aqueous phase and a precipitate of diorganotin oxide or hydroxide and then separating the tricycloalkyltin hydroxide from the organic phase.

11. A process according to claim 1 wherein a portion of said tricycloalkyltin chloride in said mixture is removed to form a residue containing the remaining portion of tricycloalkyltin chloride and said diorganotin dichloride, and said residue is treated with an aqueous base to form an organic phase comprising tricycloalkyltin hydroxide, an aqueous phase and a precipitate of diorganotin oxide or hydroxide and then separating the tricycloalkyltin hydroxide from the organic phase.

12. A process according to claim 1 wherein the organotin trichloride has been made by reaction of an organotricycloalkyltin of formula R'SnR$_3$'' with stannic chloride.

13. A process for preparing a tricycloalkyltin compound wherein an organotricycloalkyltin of formula RSnR$_3$'', wherein R is a radical selected from the group consisting of alkyl, alkenyl, aralkyl and aryl groups and R'' is a cycloalkyl group selected from the group consisting of cyclohexyl and cyclohexyl substituted by at least one inert substituent, and stannic chloride are mixed in a molar ratio of between 1.8:1 and 2.2:1 and the mixture heated at a temperature of 130°-180° C. to form a second mixture comprising tricycloalkyltin chloride and diorganotin dichloride.

14. A process according to claim 5, wherein said organotricycloalkyltin is an alkyltricyclohexyltin in which the alkyl group R has 1-8 carbon atoms, wherein R is the same as R', and wherein said reaction is at a temperature between 120° C. and 160° C. and in the absence of a liquid diluent to form a mixture comprising tricyclohexyltin chloride and dialkyltin dichloride.

15. A process according to claim 13 wherein R and R' are butyl.

16. A process according to claim 13 wherein the tricyclohexyltin chloride is crystallized from isopropanol solution of the said mixture.

17. A process according to claim 13 wherein said second mixture in solution in an inert water immiscible organic solvent is treated with an aqueous solution of base to form an organic phase comprising tricyclohexyltin hydroxide, an aqueous phase and a precipitate of dialkyltin oxide or hydroxide and then the tricyclohexyltin hydroxide is separated from said organic phase.

18. A process according to claim 14 wherein said second mixture in solution in an inert water immiscible organic solvent is treated with an aqueous solution of base to form an organic phase comprising tricyclohexyltin hydroxide, an aqueous phase and a precipitate of dialkyltin oxide or hydroxide and then the tricyclohexyltin hydroxide is separated from said organic phase.

19. A process according to claim 1 wherein R and R' are the same alkyl group of 1-8 carbon atoms.

20. A process according to claim 3 wherein the tricycloalkyltin chloride is separated from the diorganotin dichloride by preferential crystallization of the tricycloalkyltin chloride from a solution of the mixture.

21. A process according to claim 3 wherein the tricycloalkyltin chloride is separated from the diorganotin dichloride by preferential crystallization of the tricycloalkyltin chloride from an isoproponol solution of the mixture.

22. A process according to claim 3 wherein a mixture of tricycloalkyltin chloride with the diorganotin dichloride in solution in an inert liquid water immiscible organic diluent is treated with an aqueous base to form an organic phase comprising tricycloalkyltin hydroxide, an aqueous phase and a precipitate of diorganotin oxide or hydroxide and then separating the tricycloalkyltin hydroxide from the organic phase.

23. A process according to claim 3 wherein a portion of said tricycloalkyltin chloride in said mixture is removed to form a residue containing the remaining portion of tricycloalkyltin chloride and said diorganotin dichloride, and said residue is treated with an aqueous base to form an organic phase comprising tricycloalkyltin hydroxide, an aqueous phase and a precipitate of diorganotin oxide or hydroxide and then separating the tricycloalkyltin hydroxide from the organic phase.

24. A process according to claim 14 wherein R and R' are butyl.

25. A process according to claim 14 wherein the tricyclohexyltin chloride is crystallized from isopropanol solution of the said mixture.

26. A process according to claim 1 wherein said organotin trichloride is made by reacting an organotricycloalkyltin with stannic chloride in a molar ratio of between 1.8:1 and 2.2:1 at a temperature of less than 100° C. to form (i) tricycloalkyltin chloride, (ii) said organotin trichloride and (iii) excess organotricycloalkyltin, and (ii) and (iii) are then reacted at said temperature of between 110° C. and 180° C. to form additional tricycloalkyltin chloride and diorganotin dichloride.

27. A process according to claim 4 wherein said organotin trichloride is made by reacting an organotricycloalkyltin with stannic chloride in a molar ratio of between 1.8:1 and 2.2:1 at a temperature of less than 100° C. to form (i) tricycloalkyltin chloride, (ii) said organotin trichloride and (iii) excess organotricycloalkyltin, and (ii) and (iii) are then reacted at said temperature of between 110° C. and 180° C. to form additional tricycloalkyltin chloride and diorganotin dichloride.

28. A process according to claim 7 wherein said organotin trichloride is made by reacting an organotricycloalkyltin with stannic chloride in a molar ratio of between 1.8:1 and 2.2:1 at a temperature of less than 100° C. to form (i) tricycloalkyltin chloride, (ii) said organotin trichloride and (iii) excess organotricycloalkyltin, and (ii) and (iii) are then reacted at said temperature of between 110° C. and 180° C. to form additional tricycloalkyltin chloride and diorganotin dichloride.

29. A process according to claim 3 wherein the reaction is performed at 120°-160° C.

30. A process according to claim 29 wherein R is an alkyl group of 3-8 carbon atoms.

31. A process according to claim 30 wherein the tricycloalkyltin chloride is separated from the diorganotin dichloride by preferential crystallization of the tricycloalkyltin chloride from an isopropanol solution of the mixture.

32. A process according to claim 3 wherein the reaction is performed at 130°-150° C. for 1-5 hours.

33. A process according to claim 30 wherein R is butyl.

34. A process according to claim 26 wherein the organotricycloalkyltin and stannic chloride are reacted in solution below 100° C. and the subsequent reaction is carried out at 120°-160° C. in the absence of a liquid diluent.

35. A process according to claim 27 wherein the organotricycloalkyltin and stannic chloride are reacted in solution below 100° C. and the subsequent reaction is carried out at 120°-160° C. in the absence of a liquid diluent.

36. A process according to claim 28 wherein the organotricycloalkyltin and stannic chloride are reacted in solution below 100° C. and the subsequent reaction is carried out at 120°-160° C. in the absence of a liquid diluent.

37. A process according to claim 13 wherein the organotricycloalkyltin and stannic chloride are reacted in solution below 100° C. and the subsequent reaction is carried out at 120°-160° C. in the absence of a liquid diluent.

38. A process according to claim 10 wherein said diorganotin dichloride is a dialkyltin dichloride wherein each alkyl group contains 3-8 carbon atoms.

39. A process according to claim 11 wherein said diorganotin dichloride is a dialkyltin dichloride wherein each alkyl group contains 3-8 carbon atoms.

40. A process according to claim 13 wherein said second mixture of tricyclohexyltin chloride and dialkyltin dichloride, in which the alkyl groups contain 3-8 carbon atoms in solution in an inert water immiscible organic solvent, is treated with an aqueous solution of base to form an organic phase containing tricyclohexyltin hydroxide, and an aqueous phase and a precipitate of dialkyl oxide or hydroxide, and then the tricyclohexyltin hydroxide is recovered from said organic phase.

41. A process according to claim 14 wherein said second mixture of tricyclohexyltin chloride and dialkyltin dichloride, in which the alkyl groups contain 3-8 carbon atoms in solution in an inert water immiscible organic solvent, is treated with an aqueous solution of base to form an organic phase containing tricyclohexyltin hydroxide, and an aqueous phase and a precipitate of dialkyl oxide or hydroxide, and then the tricyclohexyltin hydroxide is recovered from said organic phase.

* * * * *